United States Patent [19]

Scherrer

[11] Patent Number: 5,495,043
[45] Date of Patent: Feb. 27, 1996

[54] SUBSTITUTED DI-T-BUTYLPHENOLS

[75] Inventor: Robert A. Scherrer, White Bear, Minn.

[73] Assignee: Riker Laboratories, Inc., St. Paul, Minn.

[21] Appl. No.: 435,585

[22] Filed: May 5, 1995

Related U.S. Application Data

[60] Division of Ser. No. 263,390, Jun. 22, 1994, Pat. No. 5,416,113, which is a continuation-in-part of Ser. No. 757,358, Jul. 22, 1985, abandoned.

[51] Int. Cl.$^6$ ................................................. C07C 251/24
[52] U.S. Cl. ........................ 562/440; 562/426; 562/431
[58] Field of Search ................................. 562/440, 426, 562/431

[56] References Cited

U.S. PATENT DOCUMENTS

| | | | |
|---|---|---|---|
| 3,313,848 | 4/1967 | Scherrer et al. | 260/518 |
| 3,413,313 | 11/1968 | Scherrer | 260/340.9 |
| 3,558,690 | 1/1971 | Sallmann et al. | 260/471 |
| 3,573,290 | 3/1971 | Sallmann et al. | 260/240 |
| 3,673,243 | 6/1972 | Yamamoto et al. | 260/518 R |
| 3,773,936 | 11/1973 | Shen et al. | 424/230 |
| 3,778,470 | 12/1973 | Sallman et al. | 260/518 R |
| 3,895,063 | 7/1975 | Sallman et al. | 260/571 |
| 4,070,484 | 1/1978 | Harita et al. | 424/319 |
| 4,172,151 | 10/1979 | Moore | 424/330 |
| 4,496,590 | 1/1985 | Schlegel et al. | 514/646 |
| 4,510,139 | 4/1985 | Bailey | 514/234 |
| 4,515,980 | 5/1985 | Bailey | 560/45 |
| 4,528,392 | 7/1985 | Musser et al. | 560/43 |
| 4,677,113 | 6/1987 | Bell et al. | 514/448 |
| 4,710,515 | 12/1987 | Kirk et al. | 514/563 |
| 4,714,776 | 12/1987 | Bell et al. | 562/460 |
| 4,716,178 | 12/1987 | Scherrer et al. | 514/563 |
| 4,906,662 | 3/1990 | Hashimoto et al. | 514/524 |

FOREIGN PATENT DOCUMENTS

| | | |
|---|---|---|
| 181568 | 5/1986 | European Pat. Off. . |
| 53-141234 | 12/1978 | Japan . |
| 55-145648 | 11/1980 | Japan . |
| 60-168175 | 2/1987 | Japan . |
| 7213M | 8/1969 | Switzerland . |
| 1139332 | 1/1969 | United Kingdom . |

OTHER PUBLICATIONS

Efremenko et al., Institute of Chemical Physics, Academy of Sciences of the USSR (1969).
Goldstein et al., Helv. Chem. Acta, 11, 239–245 (1928).
Chem. Abstracts 67:81701, 1967 rn=17116-90-4.

Primary Examiner—José G. Dees
Assistant Examiner—Samuel Barts
Attorney, Agent, or Firm—Gary L. Griswold; Walter N. Kirn; Robert H. Brink

[57] ABSTRACT

Novel compounds which are 2,6-di-t-butylphenols substituted on the 4 position by an anilino group, which anilino group is substituted by a carboxyl substituent, a tetrazolyl substituent or an N-methyltetrazolyl substituent, are useful antiallergic agents. Pharmaceutical compositions containing and pharmacological methods of using such compounds are also disclosed, as are synthetic intermediates for preparing such compounds. Certain of the synthetic intermediates also exhibit useful antiallergic activity.

1 Claim, No Drawings

SUBSTITUTED DI-T-BUTYLPHENOLS

CROSS-REFERENCE TO RELATED APPLICATION

This is a division of application No. 08/263,390, filed Jun. 22, 1994, now U.S. Pat. No. 5,416,113, is a continuation-in-part of application U.S. Ser. No. 757,358, filed Jul. 22, 1985, now abandoned.

TECHNICAL FIELD

This invention relates to substituted di-t-butylphenols which are anti-allergic agents. Pharmaceutical compositions containing such compounds, pharmacological methods for using such compounds and synthetic intermediates for preparing such compounds are also disclosed.

BACKGROUND OF THE INVENTION

The leukotrienes are a group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle, but also on other tissues as well. In addition, they promote mucous production, modulate vascular permeability changes and are potent inflammatory mediators in human skin. The most important compound in the second group of leukotrienes, namely dihydroxy fatty acids, is Leukotriene $B_4$. This compound is a potent chemotactic agent for neutrophils and eosinophils and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a lipoxygenase enzyme. See, for example, D. M. Bailey et al., *Ann. Rpts. Med. Chem.*, 17, 203 (1982).

RESPIRATORY CONDITIONS

Asthma. The leukotrienes are potent spasmogens of human trachea, bronchus, and lung parenchyma, and when administered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. Lipoxygenase products are also thought to be regulators of mast cell degranulation, and recent studies with human lung mast cells have suggested that lipoxygenase inhibitors (but not corticosteroids), may suppress antigen-induced mast cell degranulation. In vitro studies have shown that antigen challenge of human lung results in the release of leukotrienes and that, in addition, purified human mast cells can produce substantial amounts of leukotrienes. There is, therefore good evidence that the leukotrienes are important mediators of human asthma. Lipoxygenase inhibitors would, therefore be a new class of drugs for the treatment of asthma. See, for example, B. Samuelsson, *Science,* 220, 568–575 (1983).

SKIN DISEASES

Psoriasis. Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in non-involved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, to modulate mucous production and mucocillary clearance, and to mediate the accumulation of inflammatory leukocytes.

Leukotrienes may also mediate other diseases. These include atopic dermatitis, gouty arthritis, gall bladder spasms and ulcerative colitis. In addition, they may have a role in cardiovascular disease because Leukotrienes $C_4$ and $D_4$ act as coronary and cerebral arterial vasoconstrictors and these compounds may also have negative inotropic effects on the myocardium. In addition, the leukotrienes are important mediators of inflammatory disease through their ability to modulate leukocyte and lymphocyte function.

Many substituted di-t-butylphenols are known. Generally these compounds may be useful as antioxidants. Some of these compounds are also known to be active antiinflammatory agents.

Compounds wherein 2,6-di-t-butylphenol is substituted in the 4 position by an unsubstituted phenyl or certain simply-substituted phenyls are known antiinflammatory agents. See, for example, U.S. Pat. No. 4,172,151 and references cited therein. The compound 2,6-di(tertiary-butyl)-4-(4'-carboxyphenylimino)-2,5-cyclohexandiene-1-one is disclosed in Chemical Abstracts 67:81701n.

No compounds wherein a 2,6-di-t-butylphenol is substituted in the 4 position by an anilino group wherein such anilino group is substituted by a moiety including carboxy, tetrazolyl, N-methyl-tetrazolyl, or N-trifluoromethylsulfonyl are known.

SUMMARY OF THE INVENTION

This invention relates to certain di-t-butylphenols containing an anilino group which contain carboxy, tetrazolyl, N-methyltetrazolyl, or N-trifluoromethylsulfonyl. These compounds are useful as inhibitors of mammalian leukotriene biosynthesis. As such, these compounds are useful therapeutic agents for treating allergic conditions, particularly asthma. Pharmaceutical compositions comprising such compounds, pharmacological methods of using such compounds, and synthetic intermediates for preparing such compounds are also described. Certain of the synthetic intermediates also exhibit useful pharmacological activity as antiallergic agents.

Certain compounds of the invention are also useful as synthetic intermediates for preparing certain of the antiallergic compounds which are disclosed and claimed in U.S. Ser. No. 06/879,472 (Attorney's Docket Number FN 40825USA4C), filed of even date and commonly assigned, incorporated herein by reference. Moreover, it is believed that certain of the antiallergic compounds disclosed in said copending application are prodrugs of certain antiallergic compounds disclosed herein. For example, N-(3-carboxyphenyl)-N-(3,5-di-t-butyl-4-hydroxyphenyl)succinamic acid disclosed in said copending application is believed to possibly be a prodrug of 3-(3,5-di-t-butyl-4-hydroxyanilino)benzoic acid which is disclosed herein.

DETAILED DESCRIPTION OF THE INVENTION

The present invention relates to compounds of Formula I:

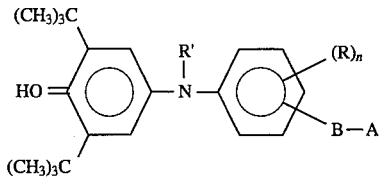

wherein R is hydrogen, lower alkyl, lower alkoxy, lower alkylthio, halogen (preferably chloro or fluoro), amino, lower alkylamino, di(lower)alkylamino, lower acylamido or hydroxy, and n is 0, 1 or 2 with the proviso that if n is 2, then all R substituents combined contain no more than 6 carbon atoms; R' is hydrogen, lower alkyl, acetyl or trifluoroacetyl; A is carboxyl, tetrazolyl, N-methyltetrazolyl or

and when A is carboxyl, B is a carbon-carbon bond, lower alkylene, lower alkenylene, lower alkylene containing one ether or thioether link in the alkylene chain, or

when A is tetrazolyl or N-methyltetrazolyl, B is a carbon-carbon bond, —CH$_2$— or

and when A is

B is a carbon-carbon bond; and derivatives of compounds wherein A is carboxyl selected from the group consisting of the lower alkyl esters, (lower)alkylamino(lower)alkyl esters, pharmaceutically acceptable (lower)alkylamino(lower)alkyl ester acid-addition salts and pharmaceutically acceptable carboxylate salts, and derivatives of compounds wherein B is tetrazolyl selected from pharmaceutically acceptable alkali metal and alkaline earth salts of the tetrazolyl moiety.

Presently preferred are compounds wherein the group —B—COOH, —B-tetrazolyl or —B-N-methyltetrazolyl is oriented para or meta to the

linking group.

Presently preferred compounds are those wherein A is carboxyl.

Presently preferred as B is a carbon-carbon bond. When B is alkylene it is preferably methylene. When B is alkenylene it is preferably ethenylene.

When R is lower alkyl, lower alkoxy or lower alkylthio, it is presently preferred to be methyl, methoxy, or methylthio respectively. The presently preferred R group is hydrogen.

By "lower" as used in connection with "alkyl" and "alkylene" is meant that such groups contain one to about four carbon atoms. Most preferred alkyl groups contain one or two carbon atoms. By "lower" as used in connection with "alkenylene" is meant that such groups contain two to about four carbon atoms.

In the compounds of Formula I wherein A is tetrazolyl, two tautomeric forms of tetrazolyl exist as is known to those skilled in the art. Tautomerism does not exist in tetrazolyl moieties where the tetrazolyl ring is substituted on a nitrogen atom by methyl. Instead, two N-methyl isomers are obtained, one in which the methyl group is in the 1-position, the other in which it is in the 2-position. All such tautomers and isomers are within the scope of this invention.

It is well known to the art that pharmaceutically acceptable salts such as alkali metal, alkaline earth, aluminum and other metal and amine salts of pharmaceutically active acids are the equivalents of the acids in terms of activity, and in some cases may even offer advantages in absorption, formulation and the like. pharmaceutically-acceptable carboxylate salts of the compounds of the invention which contain carboxyl as A are prepared in an inert atmosphere by reaction of the acid with a base and subsequent evaporation to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of the invention which contain carboxyl as A include alkyl esters, alkylaminoalkyl esters, and salts of the latter. In the ester derivatives, the hydrogen portion of the carboxylic acid group is replaced with an alkyl or substituted alkyl, preferably an alkylaminoalkyl group.

Esters of the compounds of the invention may be obtained as intermediates during the preparation of the acidic compound. In some cases, the esters may be prepared directly using standard synthetic methods. These esters may exhibit antiallergic activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group. Especially preferred are alkylaminoalkyl esters such as the dimethylaminoethyl esters which will form salts, e.g., hydrochlorides.

Ester derivatives may be obtained by alkylation of an alkali metal salt of the compound in dimethylformamide with an alkyl iodide or dialkylaminoalkylchloride, or by starting with esters instead of acids in Scheme I, Step (1) below.

Pharmaceutically acceptable alkali metal and alkaline earth salts may also be prepared of compounds of Formula I wherein A is tetrazolyl by methods known to those skilled in the art.

The preferred compounds of Formula I are 4-(3,5-di-tertiary-butyl-4-hydroxyanilino)benzoic acid, 3-(3,5-di-tertiary-butyl-4-hydroxyanilino)benzoic acid, 5-[3-(3,5-di-tertiary-butyl-4-hydroxyanilino)phenyl]tetrazole, and 5-[4-(3,5-di-tertiary-butyl-4-hydroxyanilino)phenyl] tetrazole.

Compounds of the invention may be prepared by the method of Scheme I, wherein A, R, and B are as defined above, and R' is hydrogen.

SCHEME I

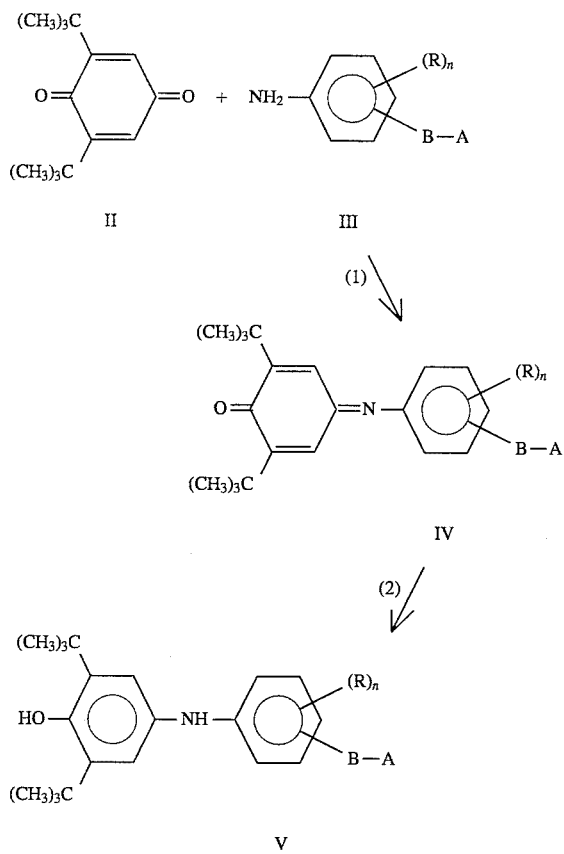

The reaction of step (1) is a Lewis acid catalyzed condensation of the known compound 2,6-di(tertiary-butyl)-p-benzoquinone (II) and a substituted aromatic amine (III). Suitable substituted aromatic amines for preparing compounds of Formula I wherein A is carboxyl are known compounds such as the aminobenzoic acids, for example, 3- and 4-aminobenzoic acid, the aminophenylacetic acids, aminophenylbutyric acids, aminophenylthioacetic acids, aminophenyloxyacetic acids, alkyl aminophenylacetates, aminophenylcinnamic acids, and the like. Similarly, suitable tetrazolyl-substituted aromatic amines for providing compounds of Formula I wherein A is tetrazolyl are known such as 5-(3- or 4-aminophenyl)tetrazoles.

Suitable Lewis acid catalysts include boron trifluoride, tin tetrachloride, titanium tetrachloride and the like.

The reaction of step (1) is carried out by combining the reactants in an inert solvent such as an ether, for example, tetrahydrofuran, and heating gently, if necessary. The products of Formula IV are novel solids which are readily isolated and may be recrystallized from polar solvents.

The reaction of step (2) is a reduction of the imino quinone system of the intermediate of Formula IV to an amino phenol. It is readily accomplished using catalytic reduction with hydrogen gas in an inert solvent when A is carboxyl. It may be carried out under neutral conditions or in the presence of base, for example, an equimolar amount of base. Suitable catalysts include platinum or palladium on charcoal. Chemical reduction can also be carried out, for example, with sodium thiosulfite, or zinc and acetic acid to provide compounds wherein A is carboxyl or tetrazolyl. Chemical reduction is preferred when B contains a double bond.

Compounds of the invention wherein R' is alkyl and A is carboxy are prepared from a compound of Formula V (obtained above) by reacting the compound with an alkyl halide, particularly an alkyl bromide or an alkyl iodide. This reaction may be carried out in a solvent such as N,N-dimethylformamide, optionally in the presence of base. When base is present, the carboxyl will generally become esterified, and therefore subsequent hydrolysis by conventional methods may be desired.

Compounds of the invention wherein R' is acetyl or trifluoroacetyl and A is carboxy are prepared from a compound of Formula V by reacting the compound with the appropriate anhydride.

Compounds of Formula I wherein A is N-methyltetrazolyl are preferably prepared by alkylating an alkali metal salt of the corresponding compound of Formula I wherein A is tetrazolyl with methyl iodide.

Compounds of Formula IV wherein A is

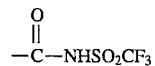

may be prepared from the corresponding compound of Formula IV wherein A is carboxy via reaction of that compound with thionyl chloride and subsequent reaction of the resulting acid chloride with sodium trifluoromethanesulfonamide. Catalytic reduction provides compounds of Formula I wherein A is

Compounds of Formula I wherein A is tetrazolyl may also be prepared by the method of Scheme II wherein R, n and B are as defined above and R' is hydrogen.

SCHEME II

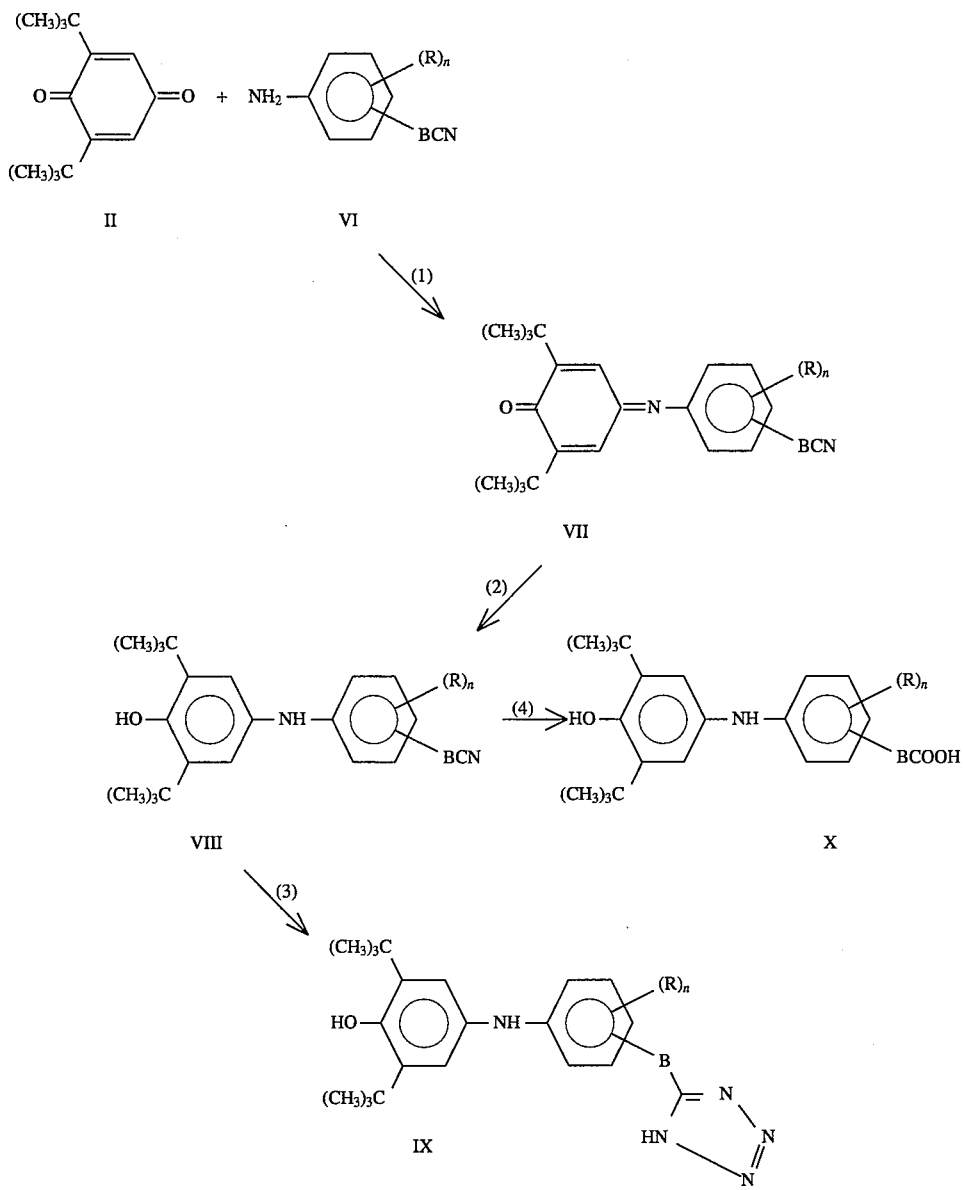

The reaction of step (1) of Scheme II is a Lewis acid catalyzed condensation similar to step (1) of Scheme I except that here an aminonitrile of Formula VI is used in place of the substituted aromatic amine used in step (1) of Scheme I. Compounds of Formula VI are known or may be prepared by conventional methods. The reaction is conducted as described in connection with step (1) of Scheme I. The product of step (1) of Scheme II is a novel intermediate of Formula VII.

The reaction of step (2) of Scheme II is a reduction of the type (and performed using the method of) step (2) of Scheme I to provide a novel intermediate of Formula VIII.

In step (3), the intermediate of Formula VIII is reacted with sodium azide in the presence of ammonium chloride and lithium chloride. The reaction is preferably conducted in N,N-dimethylformamide and is conducted under a nitrogen atmosphere and accompanied by heating.

In step (4), the intermediate of formula VIII is hydrolyzed, in an inert atmosphere, by known means such as with sodium hydroxide in aqueous ethanol, to provide compounds of Formula X.

Compounds of the invention wherein R' is alkyl and A is carboxy, tetrazolyl or N-methyltetrazolyl may be prepared by alkylating the intermediate of Formula VIII by conventional methods prior to conducting step (3) or (4).

Again, as in Scheme 1, compounds of the invention wherein R' is acetyl or trifluoroacetyl may be prepared from the compounds of Formula IX and X by reacting the compound with an appropriate anhydride as discussed previously.

Similarly, N-methyltetrazolyl derivatives may be prepared as described in connection with Scheme I above.

The anti-allergic activity of the compounds of Formula I may be demonstrated via a variety of biological assays including in vitro assays for measuring inhibition of lipoxygenase activity and leukotriene synthesis, and in vivo assays for inhibiting bronchoconstriction.

More specifically, a suitable assay for demonstrating inhibition of lipoxygenase activity by the compounds of Formula I utilizes lipoxygenase isolated from mammalian lung tissue, for example, the lung tissue of guinea pigs. An example of such an assay is that described by Ben Aziz et al., Anal. Biochem. 34, 88 (1970), incorporated herein by reference. The inhibition of lipoxygenase activity is measured by a rapid and sensitive spectrophotometric technique. The compounds of Formula I of the invention exhibit an $IC_{50}$ (the concentration at which 50% of the enzymatic activity is inhibited) of less than about 100 micromoles per liter. Preferred compounds exhibit an $IC_{50}$ of less than about 50 micromoles per liter. Most preferred compounds exhibit an $IC_{50}$ of less than about 10 micromoles per liter.

The activity of the compounds of Formula I may also be demonstrated in a more specific test for leukotriene biosynthesis inhibition. This test utilizes the cell free leukotriene biosynthesis system of M. Steinhoff et al., Biochim. Biophys. Acta. 68, 28 (1980), incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhaus et al., FEBS Letter 146, 111–114, incorporated herein by reference. Drugs are dissolved in ethanol or dimethyl sulfoxide and preincubated for five minutes. Phenidone is used as a positive control. The compounds of Formula I exhibit an $IC_{50}$ of 100 micromoles per liter or less. Preferred compounds exhibit an $IC_{50}$ less than 25 micromoles per liter, and most preferred compounds exhibit an $IC_{50}$ of less than 10 micromoles per liter.

The compounds of Formula I are relatively inactive as inhibitors of cyclooxygenase. This is important in order for there to be good in vivo antiallergic activity. A convenient in vitro method for measuring cyclooxygenase activity is an assay wherein the amount of thromboxane $B_2$ production is measured in a whole blood clotting assay. The thromboxane $B_2$ production is measured by a radioimmunoassay as described by Patrono, et al, Thromb. Res. 17, 317 (1980), incorporated herein by reference. The compounds of Formula I do not show appreciable activity at concentrations of 100 micromoles per liter.

The in vivo test used to demonstrate anti-allergic activity may be any of those known to those skilled in the art. Preferably, bronchoconstriction in sensitized guinea pigs is measured upon antigen challenge. This test is described in broad terms by Piechuta, et al., Immunology, 38, 385 (1979), incorporated herein by reference, and more specifically by Hammerbeck and Swingle, Int. Archs. Allergy Appl. Immun. 74, 84–90 (1984), incorporated herein by reference. It is used in a modified form as follows: Male Hartley guinea pigs (250–600 g) are dosed with a compound of Formula I in an amount generally about 1 to 40 mg/kg. Fifteen minutes later the animals are aerosol challenged with either water or ovalbumin at a concentration of 10 mg per ml. The animals are then placed under an inverted dessicator jar (18×14 cm) with a constant flow of air coming into the chamber from a compressed-air source to prevent hypoxia. Air flow leaving the chamber and fluctuations due to respiration are monitored through a separate outlet with a Fleisch No. 0000 pneumotachograph (available from Beckman Instruments, Inc., Schiller Park, Ill.) coupled to a Beckman Type R dynograph (available from Beckman Instruments). Aerosolization through a third outlet is made via a No. 40 DeVilbiss nebulizer (available from The DeVilbiss Company, Somerset, Pa.) for 90 seconds at 150 mm Hg. The characteristic respiratory patterns observed are summations of two air exchange processes occurring simultaneously in the chamber. One exchange process is due to inspiration and expiration of air into and out of the animal, while the other exchange process is due to the air flow into and out of the chamber due to respiratory movements. The tracing obtained is the mechanical representation of the summation of those flows. Superimposed on the tracings was a characteristic spiking ('notching'), which appears to be due to an exaggerated expiratory movement, the frequency of which correlates with the severity of the bronchoconstrictive reaction. The frequency of notching for 15 minute periods beginning 4 minutes after the beginning of the aerosol challenge is used for comparing various treatments. Effects are considered significant if the t value achieves $p<0.05$. Compounds of Formula I exhibit an intraperitoneal $ED_{40}$ of 100 mg per kg or less when tested in the above model. Preferred compounds exhibit an $ED_{40}$ of 20 mg per kg or less. Most preferred compounds of the invention exhibit an $ED_{40}$ of 10 mg per kg or less and are effective orally.

The imine intermediates of Formula IV are also active as an antiallergic agent and are believed to be reduce in Vivo to the corresponding compounds of Formula I. Specifically, 4-amino-3-(2,6-di-t-butycyclohexadienon-4-ylideneamino)benzoic acid, 4-(2,6-ditertiary-butylcyclohexadienon-4-ylideneamino)benzoic acid, 4-(2,6-di-tertiary-butylcyclohexadienon-4-ylideneamino)hippuric acid, 4-(2,6-ditertiary-butylcyclohexadienon-4-ylideneamino) cinnamic acid, 4-acetamido-3-(2,6-di-tertiary-butylcyclohexadienon-4-ylideneamino)benzoic acid, and 3-(2,6-di-tertiary-butyl-cyclohexadienon-4-ylideneamino) benzoic acid have been found to exhibit useful activity in the above described in vivo assay involving bronchoconstriction. The last compound mentioned above, when administered in vivo to a dog, has been found to be converted to the compound 3-(3,5-di-tertiary-butyl-4-hydroxyanilino)benzoic acid.

One of the preferred compounds of Formula I of the invention, namely 3-(3,5-di-tertiary-butyl-4-hydroxyanilino)benzoic acid has been found to be active as a bronchodilator in the small airways of the guinea pig as determined using the method described in L. Diamond et al., J. Appl. Physiol.: Respirat. Environ. Exercise Physiol., 43 (6), 942–948 (1977).

Thus, compounds of Formula I are antiallergic agents exhibiting in vivo activity in mammals. The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form, and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release dosage forms. Dosage forms for administration by inhalation include aerosols and sprays which may be administered in metered doses if desired.

For treating other allergies or allergic reactions, the compound of Formula I may be administered by any conventional mode, for example, orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area, salves, patches, controlled release patches, emulsions, etc. are convenient dosage forms.

For treating cardiovascular conditions any suitable mode of administration may be used.

In addition to the common dosage forms listed above, the compounds of Formula I may also be administered for various utilities and indications or for inhibiting leukotriene synthesis by conventional controlled release means and/or delivery devices.

In preparing suitable dosage forms, conventional compounding procedures and ingredients, for example, diluents, carriers, etc. may be used. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water, and the like. Similarly, the carrier or diluent can include any time delay material well known to the art, such as glyceryl monostearate or glyceryl distearate, these being useful alone or, for example, in combination with wax.

The following Examples are provided to illustrate the invention, but are not intended to limit the invention.

EXAMPLE 1

Preparation of
4-(3,5-Di-tertiary-butyl-4-hydroxyanilino)benzoic Acid

Step A

A mixture of 22 g (0.10 mole) of 2,6-di(tertiary-butyl)-p-benzoquinone, 13.7 g (0.10 mole) of 4-aminobenzoic acid, 175 ml of tetrahydrofuran and 1 ml of boron trifluoride: diethyl ether complex was heated on a steam bath for 1.25 hours. The mixture was allowed to cool to about 20° C over 16 hours under a nitrogen atmosphere. Evaporation provided a solid which was washed with hexane and recrystallized from ethanol to provide orange solid 2,6-di(tertiary-butyl)-4-(4'-carboxyphenylimino)-2,5-cyclohexadien- 1-one, m.p. 305°–309° C. Analysis: Calculated for $C_{21}H_{25}NO_3$: % C, 74.3; % H, 7.4; % N, 4.1; Found: % C, 74.2; % H, 7.4; % N, 4.1.

Step B

To a solution of 5.0 g (0.0147 mole) of 2,6-di(tertiary-butyl)-4-(4'-carboxyphenylimino)-2,5-cyclohexadien-1-one in 300 ml of ethanol was added 0.25 g of 5 percent palladium on charcoal. It was subjected to hydrogenation in a Paar apparatus and filtered. This solvent was removed by evaporation under vacuum and the residue was recrystallized from a 5:2 (v/v) ethanol-water mixture to provide light-orange crystals of 4-(3,5-di-tertiary-butyl-4-hydroxyanilino)benzoic acid, m.p. 241°–243° C. Analysis: Calculated for $C_{21}H_{27}NO_3$: % C, 73.9; % H, 8.0; % N, 4.1; Found: % C, 73.9; % H, 7.9; % N, 3.8.

EXAMPLE 2

Using the method of Example 1, 2,6-di(tertiary-butyl)-p-benzoquinone was reacted with 3-aminobenzoic acid to provide red-orange crystals of 2,6-di(tertiary-butyl)- 4-(3'-carboxyphenylimino)-2,5-cyclohexadien-1-one, m.p. 230°–231° C. Analysis: Calculated for $C_{21}H_{25}NO_3$: % C, 74.3; % H, 7.4; % N, 4.1; Found: % C, 74.1; % H, 7.6; % N, 3.7.

EXAMPLES 3–6

Using the general method of Example 1, the aminobenzene starting materials of Formula III, shown in Table I below were reacted with 2,6-di(tertiary-butyl)-p-benzoquinone to provide the imine products indicated in Table I.

TABLE I

| Example No. | Starting Material of Formula III | Product of Formula IV (m.p. in °C.) |
|---|---|---|
| 3 | 4-aminophenylacetic acid | 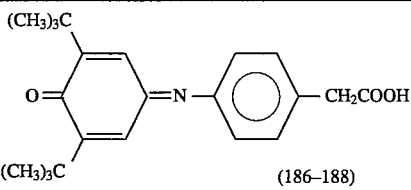 (186–188) |
| 4 | 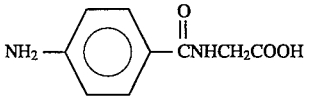 | 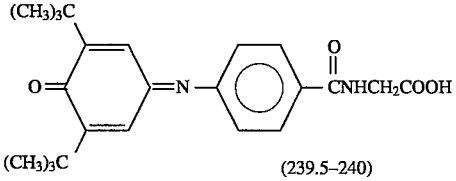 (239.5–240) |
| 5 | 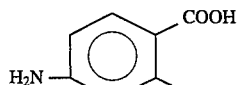 | 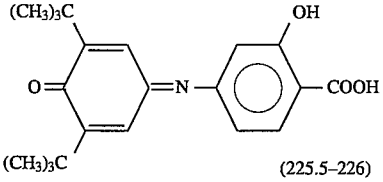 (225.5–226) |

TABLE I-continued

| Example No. | Starting Material of Formula III | Product of Formula IV (m.p. in °C.) |
|---|---|---|
| 6 | H₂N-C₆H₃(CH₃O)-COOH (3-amino-4-methoxybenzoic acid structure) | 2,6-di(tert-butyl)-4-(3'-carboxy-4'-methoxyphenylimino)-2,5-cyclohexadien-1-one (226.5–228) |

EXAMPLE 7

To a mixture of 200 ml of ethanol and 23.8 g (0.0701 mole) of 2,6-di(tertiary-butyl)-4-(4'-carboxylphenylimino)-2,5-cyclohexadien-1-one was added 2.9 g (0.072 mole) of sodium hydroxide in 20 ml of water. To this mixture was added 1.0 g of 10% palladium on charcoal, followed by the addition of 50 ml of water. The mixture was reduced by agitating on a Paar apparatus for about 16 hours. Celite was added to the mixture, and the mixture was filtered through a bed of celite. The mixture was acidified with 6N hydrochloric acid, and the resulting yellow solid precipitate was collected by filtration to provide 4-[3,5-di(tertiary-butyl)-4-hydroxyanilino]benzoic acid, m.p. 241°–242° C.

EXAMPLE 8

To a mixture of 200 ml of ethanol and 25.0 g (0.0736 mole) of 2,6-di(tertiary-butyl)-4-( 4'-carboxyphenylimino)-2,5-cyclohexadien-1-one and 12 g (0.087 mole) of potassium carbonate warmed on a steam bath was added 1.0 g of palladium on charcoal. The mixture was reduced using a Paar apparatus for 2 hours. The mixture was diluted with 300 ml of water, filtered through celite, and the filtrate acidified with 6N hydrochloric acid. The yellow solid precipitate was collected by filtration to provide 4-[3,5-di(tertiary-butyl)-4-hydroxyanilino]benzoic acid, m.p. 241°–242° C.

EXAMPLES 9–13

Using the general method of Example 7 or 8 the imine intermediates obtained in Example 2–6 were reduced to provide compounds of Formula I shown in Table II below:

TABLE II

| Example No. | Intermediate of Formula IV | Product of Formula I | Melting Point in °C. | Hydrogenation Method used |
|---|---|---|---|---|
| 9 | Example 3 | 3,5-di(tert-butyl)-4-hydroxyphenyl-NH-C₆H₄-CH₂COOH | 186–188 | Example 8 |
| 10 | Example 4 | 3,5-di(tert-butyl)-4-hydroxyphenyl-NH-C₆H₄-C(O)NHCH₂C(O)OH | 202.5–203.5 | Example 7 |
| 11 | Example 5 | 3,5-di(tert-butyl)-4-hydroxyphenyl-NH-C₆H₃(OH)-COOH | 177.5–178 | Example 7 |
| 12 | Example 6 | 3,5-di(tert-butyl)-4-hydroxyphenyl-NH-C₆H₃(OCH₃)-COOH | 239.5–240 | Example 7 |

TABLE II-continued

| Example No. | Intermediate of of Formula IV | Product of Formula I | Melting Point in °C. | Hydrogenation Method used |
|---|---|---|---|---|
| 13 | Example 2 | (CH₃)₃C, HO—⟨⟩—NH—⟨⟩—COOH, (CH₃)₃C | 250.5–252 | Example 7 |

EXAMPLE 14

A mixture of a solution of 6.3 g (0.018 mole) of 4-[3,5-di-(tertiary-butyl)-4-hydroxyanilino]phenylacetic acid in 10 ml of N,N-dimethylformamide and 5 g (0.036 mole) of potassium carbonate was heated on a steam bath until gas evolution ceased. The mixture was allowed to cool to ambient temperature, and 5 milliliters of methyl iodide were then added. The mixture was heated at its boiling temperature and 5 ml aliquots of methyl iodide were added at 20, 45 and 60 minutes. After the mixture had evaporated, the residue was taken up in water and 2N sodium hydroxide solution was added. The mixture was warmed, and the insoluble residue of methyl 4-[3,5-di(tertiary-butyl)- 4-hydroxy-N-methyl-anilino] phenylacetate was separated by filtration. The residue was suspended and partially dissolved in 50 ml of methanol, and 10 ml of 2.5N sodium hydroxide solution was added. The mixture was stirred for about 16 hours, diluted with 300 ml of water and 300 ml of diethyl ether, and was then further diluted with about 100 ml of hexane. The mixture was acidified with dilute hydrochloric acid and the aqueous phase was discarded. The organic phase was washed first with 10% sodium bicarbonate solution and then with 5% sodium carbonate solution. The product remained in the organic phase as the sodium salt. The organic phase was acidified with 10% aqueous hydrochloric acid and washed with sodium chloride solution, followed by drying. Evaporation provided a residue which was extracted with 20 ml of boiling benzene. Hexane (6 ml) was added, and the light yellow solid was recrystallized first from 80% aqueous ethanol, and then from benzene to provide fine yellow needles of 4-[3,5-di(tertiary-butyl)-4-hydroxy-N-methylanilino]phenylacetic acid, m.p. 81°–182.5° C. Analysis: Calculated for $C_{23}H_{31}NO_3$: % C, 74.8; % H, 8.5; % N, 3.8; Found: % C, 74.8; % H, 8.6; % N, 3.6.

EXAMPLE 15

A solution of 3.4 g (0.010 mole) of 4-(3,5-di-tertiary-butyl-4-hydroxyanilino)benzoic acid (prepared in Example 1) in 35 ml of N,N-dimethylformamide and 3.5 ml of methyl iodide was heated at 95° C. for about 48 hours under nitrogen. The reaction mixture was poured into cold water and the resulting solid was collected and then taken up in chloroform. The chloroform solution was filtered, washed with water, dried with magnesium sulfate and evaporated to give a tan solid. This material was recrystallized first from benzene and then from a mixture of ethanol and water to give 1.5 g of white crystalline 4-(3,5-di-tertiary-butyl-4-hydroxy-N-methylanilino)benzoic acid, m.p. 240°–244° C. Analysis: Calculated for $C_{22}H_{29}NO_3$: % C, 74.3; % H, 8.2; % N, 3.9. Found: % C, 74.4; % H, 8.3; % N, 3.5.

EXAMPLE 16

A mixture of 2.0 g (0.00589 mole) of 2,6-di(tertiary-butyl)-4-(4-carboxyphenylimino)-2,5-cyclohexadien- 1-one and 2.5 g of sodium thiosulfite in 25 ml of 1N sodium hydroxide solution and a few ml of diethyl ether were stirred at 20° C. After one hour of stirring the mixture was heated on a steam bath while adding 1.5 g of sodium thiosulfite and enough sodium hydroxide to make the solution alkaline. After one hour the solution was acidified with 6N hydrochloric acid. The precipitate separated by filtration to provide a light orange solid was about 50% 3-[3,5-di(tertiary-butyl)-4-hydroxyanilino]benzoic acid according to thin layer chromatographic and infrared spectral analyses.

EXAMPLES 17–19

Using the general method of Example 1, the aminobenzene starting materials of Formula III below were reacted with 2,6-di(tertiary-butyl)-p-benzoquinone to provide the imine products indicated in TABLE III.

TABLE III

| Example Number | Starting Material of Formula III | Product of Formula IV (m.p. in °C.) | Melting Point in °C. |
|---|---|---|---|
| 17 | H₂N—⟨⟩—CO₂H, CH₃ | (CH₃)₃C, O=⟨⟩=N—⟨⟩—CO₂H, (CH₃)₃C, CH₃ | (241–245) |

TABLE III-continued

| Example Number | Starting Material of Formula III | Product of Formula IV | Melting Point (m.p. in °C.) |
|---|---|---|---|
| 18 | H₂N—⌬(CO₂H)—OH | (CH₃)₃C substituted cyclohexadienone =N—⌬(CO₂H)—OH | (249–259) |
| 19 | H₂N—⌬(CO₂H)—Cl | (CH₃)₃C substituted cyclohexadienone =N—⌬(CO₂H)—Cl | (195–199) |

EXAMPLE 20

To a mixture of 225 ml ethanol and 13.6 g (0.038 mole) of 2,6-di(tertiary-butyl)-4-(5'-carboxy-2'-methylphenylimino)- 2,5-cyclohexadiene-1-one (from Example 18) was added 1 g of 5% palladium on charcoal (50% water wet). The mixture was reduced by agitating on a Paar apparatus for 2 hours. The mixture was filtered through celite to remove the catalyst and the filtrate was concentrated on a rotary evaporator to give 13.0 g of a light orange solid, m.p. 229°–233° C. This material was recrystallized from aqueous ethanol to give 10.8 g orange crystalline solid m.p. 234°–239° C. This material was in turn recrystallized from benzene to give 9.6 g pale orange solid 3-(3,5-di-tertiary-butyl-4-hydroxyanilino)-4-methylbenzoic acid, m.p. 234°–239° C. Analysis: Calculated for $C_{22}H_{29}NO_3$: % C 74.3; % H 8.2; % N 3.9. Found: % C, 74.3; % H, 8.2; % N 3.8.

EXAMPLES 21–22

Using the general method of Example 20, the imine intermediates obtained in Examples 18 and 19 were reduced to provide compounds of Formula I shown in TABLE IV below:

TABLE IV

| Example Number | Product of Formula I | (m.p. in °C.) |
|---|---|---|
| 21 | HO—⌬((CH₃)₃C)₂—NH—⌬(CO₂H)—Cl | (200.5–201.5) |
| 22 | HO—⌬((CH₃)₃C)₂—NH—⌬(CO₂H)—OH | (234–238) |

EXAMPLE 23

A mixture of 22.0 g (0.10 mole) of 2,6-di(tertiary-butyl)-p-benzoquinone, 19.0 g (0.105 mole) of (4-aminophenyl)thioacetic acid, 100 ml of tetrahydrofuran and 1 ml of boron trifluoride: diethyl ether complex was heated at gentle reflux, with stirring, for 1.5 hours. The reaction mixture was concentrated under a nitrogen gas flow to a volume of 75 ml. The concentrate was diluted with 250 ml ethanol and 1 g of palladium on charcoal was added. This mixture was hydrogenated on a Paar apparatus for 12 hours, then filtered through celite to remove the catalyst. The filtrate was concentrated to give 33.7 g of an oil. The oil was taken up in diethyl ether. This solution was washed with dilute (about 10%) hydrochloric acid, then dried and evaporated to give 18.4 g of a gummy solid. This material was recrystallized from 5:6 benzene:hexane to give 6.3 g of pink solid 4-(3, 5-di-tertiary-butyl-4-hydroxyanilino)phenylthioacetic acid, m.p. 136.5°–137.5° C. Analysis: Calculated for $C_{22}H_{29}NO_3S$: % C, 68.2; % H, 7.5; % N, 3.6. Found: % C, 68.3; % H, 7.7; % N, 3.3.

EXAMPLE 24

A mixture of 22.5 g (0.105 mole) of 2,6-di-tertiary-butyl-p-benzoquinone, 11.8 g (0.10 mole) of anthranilonitrile, 50 ml of tetrahydrofuran and 1 ml of boron trifluoride:diethyl ether complex was heated at gentle reflux for 2 hours. Heating was continued for an additional 2 hours under a stream of nitrogen gas to concentrate the mixture. The concentrated mixture was diluted with 50 ml of ethanol, warmed to effect complete dissolution, and then allowed to cool. The precipitate was collected, rinsed with cold 4:1 methanol:water, and oven dried to give 23.6 g of orange crystals of 2,6-di-tertiary-butyl-4-(2'-cyanophenylimino)-2, 5-cyclohexadien- 1-one, m.p. 109°–110.5° C.

To a mixture of 15.0 g (0.0468 mole) of 2,6-di-tertiary-butyl-4-(2'-cyanophenylimino)-2,5-cyclohexadien- 1-one (obtained above) and 200 ml of ethanol was added 1 g of palladium on charcoal. The mixture was hydrogenated on a Paar apparatus for 10 minutes. The solvent was decanted off, then the residual solid was dissolved in chloroform. The chloroform solution was mixed with ethanol, filtered, and concentrated to give 14.6 g of tan solid, m.p. 170°–173° C. A portion (1.9 g) of this material was recrystallized from ethanol to give pale orange prisms of the novel compound 2-(3,5-di-tertiary-butyl- 4-hydroxyanilino)benzonitrile, m.p. 171.5°–172.5° C. Analysis: Calculated for $C_{21}H_{26}N_2O$: % C 78.2; % H 8.1; % N 8.7. Found: % C 78.3; % H 8.3; % N 8.6.

A mixture of 5.8 g (0.018 mole) 2-(3,5-di-tertiary-butyl-4-hydroxyanilino)benzonitrile, 40 g of 50% sodium hydroxide and 100 ml of ethanol was heated at gentle reflux for 3 hours. The reaction mixture was poured onto a mixture of 100 ml of 6N hydrochloric acid and ice. The precipitate was collected and dried in a vacuum oven to give 5.8 g of yellow solid, m.p. 217°–219° C. This material was recrystallized from a mixture of ethanol and water to give 4.9 g of light orange needles of N-(3,5-di-tertiary-butyl- 4-hydroxyphenyl)anthranilic acid, m.p. 220.5°–221.5° C. Analysis: Calculated for $C_{21}H_{27}NO_3$: % C 73.9; % H 8.0; % N 4.1; Found: % C 74.1; % H 8.1; % N 4.0.

EXAMPLES 25–26

Using the general method of Example 1 the starting materials of Formula VI shown in TABLE V below were reacted with 2,6-di(tertiary-butyl)-p-benzoquinone to provide the imine products indicated in TABLE V.

EXAMPLE 27

Using the method of Example 20, 8.0 g of 2,6-di-t-butyl-4-(3'-cyanophenylimino)-2,5-cyclohexadien-1-one (from Example 26) was converted to 3-(3,5-di-t-butyl- 4-hydroxyanilino)benzonitrile, m.p. 150°–153° C.

EXAMPLE 28

Eight g (0.025 mole) of 3-(3,5-di-t-butyl-4-hydroxyanilino)benzonitrile (from Example 27), 4.9 g (0.075 mole) of sodium azide, 4.0 g (0.075 mole) of ammonium chloride, 1.06 g (0.025 mole) of lithium chloride and 60 ml of N,N-dimethylformamide were combined under a nitrogen atmosphere and heated at 110° C. for 48 hours. The reaction mixture was poured into cold 6N hydrochloric acid and a gummy solid precipitated out. The supernatant was decanted off and the residue dissolved in ethanol. The ethanol solution was diluted with water and a pink solid was collected. This material was recrystallized from a mixture of ethanol and water to give 5.97 g of 5-[3-(3,5-di-t-butyl-4-hydroxyanilino)phenyl]tetrazole, m.p. 231°–233° C. Analysis: Calculated for $C_{21}H_{27}N_5O$: % C, 69.0; % H, 7.4; % N, 19.2; Found: % C, 68.4; % H, 7.6; % N, 18.8.

EXAMPLE 29

Using the method of Example 20, 10 g of 2,6-di-t-butyl-4-(4'-cyanophenylimino-2,5-cyclohexadien-1-one (from Example 27) was hydrogenated to give 4-(3,5-di-t-butyl-4-hydroxyanilino)benzonitrile.

EXAMPLE 30

Seven g (0.0205 mole) of 4-(3,5-di-t-butyl-4-hydroxyanilino)benzonitrile (from Example 29), 4.01 g (0.0615 mole) of sodium azide, 3.29 g (0.0615 mole) of ammonium chloride and 50 ml of N,N-dimethylformamide were combined and heated first at 105° C. for 20 hours and then at 150° C. for 9 hours. The reaction mixture was diluted with diethyl ether and water and acidified with 6N HCl. The ether phase was washed with sodium chloride solution, dried over sodium sulfate, and concentrated to an oil under a stream of nitrogen. The crude product was treated with chloroform and hexane to convert it from an oil to a solid. The solid was recrystallized from a mixture of ethanol and water to give 2.6 g of light orange needles of 5-[4-(3,5-di-t-butyl- 4-hydroxyanilino)phenyl]tetrazole, m.p. 224°–225° C. Analysis: Calculated for $C_{21}H_{27}N_5O \cdot C_2H_5OH$: % C, 67.1; % H, 8.1; % N, 17.0; Found: % C, 67.1; % H, 8.2; % N, 16.9.

EXAMPLE 31

Preparation of N,N-Dimethyl-2-aminoethyl 3-(3,5-Di-tertiary-butyl-4-hydroxyanilino)benzoate Under a nitrogen atmosphere, 6.0 g (0.0176 mole) of 3-(3,5-di-tertiary-butyl-4-hydroxyanilino)benzoic acid (from Example 13) and 2.53 g (0.0176 mole) of 2-dimethylaminoethyl chloride hydrochloride were dissolved in 17 ml of N,N-dimethylformamide. To this mixture was added 4.9 ml (0.035 mole) of triethylamine and the reaction was heated at 100° C for 25 hours. The reaction temperature was then raised to 120° C. and heating was continued for an additional 28 hours. The reaction mixture was diluted with 10 ml of diethyl ether, then filtered to remove triethylamine hydrochloride. The filtrate was diluted with additional diethyl ether and then shaken with cold 10% hydrochloric acid. A middle layer contained most of the product hydrochloride. It was diluted with water and ether, and basified with solid sodium carbonate. The ether extract was washed with saturated aqueous sodium chloride and then concentrated to give

| Example Number | Starting Material of Formula VI | Product of Formula I | (m.p. in °C.) |
|---|---|---|---|
| 25 | $NH_2$-phenyl-CN (ortho) | $(CH_3)_3C$-substituted cyclohexadienone =N-phenyl-CN | (102.5–103) |
| 26 | $NH_2$-phenyl-CN (para) | $(CH_3)_3C$-substituted cyclohexadienone =N-phenyl-CN | (140–142) |

1.7 g of a tan solid, m.p. 119°–120° C. This material was recrystallized first from 20 ml of cyclohexane and then from a mixture of 10 ml of ethanol and 3 ml of water to give 1.48 g of light yellow prisms of N,N-dimethyl-2-aminoethyl 3-(3,5-di-t-butyl-4-hydroxyanilino)benzoate m.p. 123°–124° C. Analysis: Calculated for $C_{25}H_{36}N_2O_3$: % C, 72.8; % H, 8.8; % N, 6.8. Found: % C, 73.0; % H, 8.8; % N, 6.7.

EXAMPLE 32

Preparation of N-Acetyl-3-(3,5-di-t-butyl-4-hydroxyanilino)benzoic Acid

A mixture of 5.6 g of 3-(3,5-di-t-butyl-4-hydroxyanilino)benzoic acid (from Example 13) and 15 ml of acetic anhydride was heated under a nitrogen atmosphere at 70°–120° C. for about 90 minutes. The mixture was cooled to 80° C., 5 drops of pyridine were added and the reaction was reheated to 120° C. for 10 minutes. An additional 0.25 ml of pyridine was added at about 80° C., followed by the gradual addition of 10 ml of water to hydrolyze the excess acetic anhydride and the mixed anhydride of the product. Heating was continued until a precipitate formed. The reaction mixture was allowed to cool to room temperature, and the precipitate was then collected, rinsed with a cold mixture of methanol and water, and dried to give 4.3 g of off-white solid m.p. 204°–205.5° C. This material was recrystallized first from a mixture of 30 ml of ethanol and 5 ml of water, and then from a mixture of 30 ml of isopropanol and 5 ml of hexane to give 3.3 g of white solid N-acetyl-3-(3,5-di-t-butyl- 4-hydroxyanilino)benzoic acid m.p. 214.5°–215.5° C. Analysis: Calculated for: $C_{23}H_{29}NO_4 \cdot \frac{1}{2}(CH_3)_2CHOH$: % C, 71.2; % H, 8.0; % N 3.4. Found: % C, 71.4; % H, 8.1; % N, 3.2.

EXAMPLE 33

Preparation of N-Trifluoroacetyl-3-(3,5-di-t-butyl-4-hydroxyanilino)benzoic Acid 2.96 g of 3-(3,5-di-t-butyl-4-hydroxyanilino)benzoic acid (from Example 13) was slurried in 10 ml of trifluoroacetic anhydride. After several minutes, the reaction boiled (40° C.) and then became clear. The reaction mixture was poured into a mixture of ice and water and the resulting solid was collected and dried. This material was recrystallized from a mixture of 40 ml of ethanol and 12 ml of water to give 3.07 g of white crystalline N-trifluoroacetyl- 3-(3,5-di-t-butyl-4-hydroxyanilino)-benzoic acid m.p. 181° C. Analysis: Calculated for $C_{23}H_{26}F_3NO_4$: % C, 63.1; % H, 6.0; % N, 3.2. Found: % C, 63.0; % H, 6.4; % N, 2.8.

EXAMPLE 34

A mixture of 22.0 g (0.10 mole) of 2,6-di-t-butyl-p-benzoquinone, 15.2 g (0.10 mole) of 3,4-diaminobenzoic acid, 50 ml of tetrahydrofuran and 1 ml of boron trifluoride etherate was heated at about 55° C. for 45 minutes. The reaction mixture was diluted with 100 ml of ethanol and 40 ml of water and was then allowed to stand overnight at 25° C. The resulting precipitate was collected and dried to give 31.8 g of deep red solid 4-amino-3-(3,5-di-t-butylcyclohexadiene- 4-ylideneamino)benzoic acid, m.p. 253°–253.5° C. Analysis: Calculated for $C_{21}H_{26}N_2O_3$: % C, 71.2; % H, 7.4, % N, 7.9. Found: % C, 71.0; % H, 7.5; % N, 7.8.

A mixture of 21.1 g of 4-amino-3-(3,5-di-t-butylcyclohexadienon- 4-ylideneamino)-benzoic acid, 50 ml of ethanol, 20 ml of water, 2.4 g of sodium hydroxide and 0.03 g of 5% palladium on charcoal catalyst was placed on a Paar apparatus. After 16 hours the hydrogen uptake was complete. Under a nitrogen atmosphere, the reaction was filtered into 3 ml of 6N hydrochloric acid. The filtrate was diluted with water and additional hydrochloric acid. The resulting precipitate was collected, rinsed with a cold mixture of methanol and water and dried to give 15.5 g of a lavender solid, m.p. 261.5°–262° C. Two g of this material was stirred with 150 ml of warm ethyl acetate, and was then filtered. The filtrate was diluted with 25 ml of hexane. The resulting precipitate was collected and dried to give 0.3 g of light purple crystalline 4-amino-3-(3,5-di-t-butyl- 4-hydroxyanilino)benzoic acid m.p. 261°–261.5° C. Analysis: Calculated for $C_{21}H_{28}N_2O_3$: % C, 70.8; % H, 7.9; % N, 7.9. Found: % C, 70.8; %}{, 7.9; % N, 7.6.

EXAMPLE 35

Under a nitrogen atmosphere, a suspension of 2.0 g of 5-[4-(3,5-di-tertiary-butyl-4-hydroxyanilino)phenyl]tetrazole, prepared in Example 30, and 2.0 g of potassium carbonate in 4 ml of N,N-dimethylformamide was warmed to obtain a deep red solution of the potassium salt. Approximately 4 g of methyl iodide was added and the reaction was warmed for several minutes until the color lightened. An additional 4 g of methyl iodide was added and the reaction mixture was heated at a gentle reflux for about five minutes. The reaction mixture was cooled, diluted with diethyl ether, and poured into dilute hydrochloric acid. The ether phase was washed with water and brine, dried with sodium sulfate, and evaporated to give 1.88 g of a red-brown solid. This material was recrystallized from a mixture of benzene and hexane to give 0.53 g of light yellow-tan Material #1, m.p. about 205° C. A solid precipitated from the mother liquor of Material #1. It was collected to give 0.73 g of pink Material #2, m.p. 172°–175.5° C. Material #1 was recrystallized from a mixture of 20 ml of ethanol and 5 ml of water to give 0.34 g of light brown granules, m.p. 218°–221° C. Material #2 was stirred with 50 ml of ethanol, then filtered to remove some undissolved material. The filtrate was diluted with 20 ml of water to give 0.56 g of pale pink leaflets, m.p. 175.5°–177° C. By proton NMR analysis, Material #1 is believed to be the 1-methyltetrazole and Material #2 the 2-methyltetrazole. The delta-values are 4.15 and 4.36 ppm, respectively, for the two products.

EXAMPLE 36

Using the method of Example 1, 4-aminobenzylcyanide was reacted with 2,6-di-tertiary-butyl-p-benzoquinone to give 2,6-di-tertiary-butyl-4-(4'-cyanomethylphenylimino)-2,5-cyclohexadiene-1-one, m.p. 26.5°–127.5° C. Following the reduction method of Example 1, Step B, the corresponding anilino phenylacetonitrile, m.p. 146°–147° C., was obtained. This was converted to 5-[4-(3,5-di-t-butyl-4-hydroxyanilino)benzyl]tetrazole, m.p. 212°–214° C. (dec), following the method of Example 30, but carried out at 110° C. for 48 hours.

EXAMPLE 37

Example 36 was rerun using tin tetrachloride instead of boron trifluoride as the catalyst. Thin layer chromatography using two different systems showed that the reaction mixture contained the desired 2,6-di-tertiary-butyl- 4-(4'-cyanomethylphenylimino)-2,5-cyclohexadien-1-one.

EXAMPLE 38

Example 36 was rerun using titanium tetrachloride instead of boron trifluoride as the catalyst. Thin layer chromatography using two different systems showed that the reaction mixture contained the desired 2,6-di-tertiary-butyl- 4-(4'-cyanomethylphenylimino)-2,5-cyclohexadiene-1-one.

EXAMPLE 39

A mixture of 1.70 g (0.005 mole) of 3-(3,5-di-tertiary-butyl-4-hydroxyanilino)benzoic acid (prepared in Example 13) and 50 ml of hot isopropyl alcohol was filtered to remove a small amount of insoluble material. The resulting solution was deoxygenated with a stream of nitrogen gas. Uner a nitrogen atmosphere, a solution of 0.44 g (0.005 mole) of morpholine in 1.5 ml of isopropyl alcohol was added with rapid stirring. Evaporation provided a solid which was recrystallized from a mixture of isopropyl alcohol and isopropyl ether to give solid morpholinium-3-(3,5-di-tertiary-butyl-4-hydroxyanilino)benzoate, m.p. 147°–150° C. Analysis: Calculated for $C_{21}H_{27}NO_3C_4H_9NO$: % C, 70.1; % H, 8.5; % N, 6.5; Found: % C, 9.8; % H, 8.5; % N, 6.4.

EXAMPLE 40

A suspension of 6.68 g (0.0196 mole) of 2,6-di-tertiary-butyl-4-(3'-carboxyphenylimino)-2,5-cyclohexadien- 1-one (prepared in Example 2) in 20 ml of benzene and 3 ml of thionyl chloride was heated at reflux with stirring until gas evolution had ceased. Evaporation provided an oil which was diluted with a small amount of tetrahydrofuran and added dropwise to a suspension of 3.7 g of anhydrous 5-aminotetrazole in 25 ml of tetrahydrofuran containing 1.5 ml of pyridine. The reaction mixture was allowed to stand at room temperature under a nitrogen atmosphere for 16 hours. The reaction mixture was diluted to a volume of 500 ml with diethyl ether, and was then filtered. The filter cake was rinsed with diethyl ether and resuspended in 300 ml of diethyl ether and filtered again. The combined filtrates were evaporated to give 4.7 g of an orange solid, m.p. 241°–244° C. One g of this material was recrystallized from ethanol to provide 0.3 g of orange 3-(2,6-di-tertiary-butylcyclohexadienon-4-ylideneamino)-N-( 5-tetrazolyl)benzamide, m.p. 271.5° C. (dec.). Analysis: Calculated for $C_{22}H_{26}N_6O_2$: % C, 65.0; % H, 6.4; % N, 20.7; Found: % C, 65.1; % H, 6.4; % N, 20.5.

A of mixture of 3.1 g 3-(2,6-di-tertiary-butylcyclohexadienon- 4-ylideneamino)-N-(5-tetrazolyl)benzamide, 200 ml of tetrahydrofuran, and 0.7 g of palladium on charcoal catalyst was placed on a Paar apparatus. Hydrogenation was complete after two hours. Under a nitrogen atmosphere, the reaction was filtered to remove the catalyst. The filtrate was evaporated to give 4.3 g of a sticky yellow solid which was recrystallied from a mixture of 130 ml acetic acid and 20 ml of water to give 1.6 g of yellow solid 3-(3,5-di-tertiary-butyl-4-hydroxyanilino)-N $^1$-(5-tetrazolyl)benzamide, m.p. 282°–283° C. Analysis: Calculated for $C_{22}H_{28}N_6O_2$: % C, 64.7; % H, 6.9; % N, 0.6; Found: % C, 64.6; % H, 6.8; % N, 20.2.

EXAMPLE 41

A mixture "of 5.51 g (0.025 mole) of 2,6-di-tertiary-butyl-p-benzoquinone, 4.54 g (0.027 mole) of 3-(4-aminophenyl-)propionic acid, 50 ml of tetrahydrofuran and 0.25 ml of boron trifluoride etherate was heated on a steam cone under a slow stream of nitrogen for two hours. The resulting solid was triturated with hexane, collected, rinsed with hexane and recrystallized from a mixture of ethyl acetate and hexane to give 5.1 g yellow 3-[4-(2,6-di-tertiary-butylcyclohexadienon- 4-ylideneamino)phenyl]propionic acid, m.p. 165°–167° C. Analysis: Calculated for $C_{23}H_{29}NO_3$: % C, 75.2; % H, 8.0; % N, 3.8; Found % C, 74.8; % H, 7.9; % N, 3.7.

A mixture of 4.0 g of 3-[4-(2,6-di-tertiary-butylcyclohexadienon- 4-ylideneamino)phenyl]propionic acid, 200 ml of ethanol of 0.1 g of 10% palladium on charcoal catalyst was placed on a Paar apparatus. Hydrogen uptake was complete after 30 minutes. Under a nitrogen atmosphere, the reaction mixture was filtered to remove catalyst. The filtrate was evaporated to give an oil which was coevaporated with hexane to remove all traces of ethanol and then triturated with hexane to give a light orange crystalline solid. This solid was recrystallized from a mixture of ethanol and water to give 3.1 g 3-[N-(3,5-di-tertiary-butyl-4-hydroxyphenyl)-4-aminophenyl] propionic acid, m.p. 140°–142° C. Analysis: Calculated for $C_{23}H_{31}NO_3$: % C, 74.8; % H, 8.5; % N, 3.8; Found: % C, 74.7; % H, 8.3; % N, 3.9.

EXAMPLE 42

A mixture of 22.0 g (0.10 mole) of 2,6-di-tertiary-butyl-p-benzoquinone, 10.9 g (0.01 mole) of m-aminophenol, 50 ml of tetrahydrofuran and 0.5 ml of boron trifluoride etherate was stirred at room temperature for about one hour. The reaction mixture was diluted with diethyl ether, and the ether solution was extracted with 10% hydrochloric acid and dried over magnesium sulfate. Evaporation gave an orange-red solid. This material was dissolved in a mixture of diethyl ether and methylene chloride. The solution was filtered, and was then evaporated to give 29.1 g orange-red solid. This material was recrystallized from a mixture of 50 ml of benzene and 100 ml of hexane to give 17.0 g of orange-red crystals, m.p. 162°–169° C. This material (2.5 g) was recrystallized first from a mixture of 15 ml benzene and 10 ml of hexane and then from a mixture of 10 ml of isopropanol and 7 ml of water to give 1.3 g of orange crystalline 3-(2,6-di-tertiary-butylcyclohexadienon- 4-ylideneamino)phenol, m.p. 169°–169.5° C. Analysis: Calculated for $C_{20}H_{25}NO_2$: % C, 77.1; % H, 8.1; % H, 4.5; Found: % C, 77.2; % H, 8.0; % N, 4.6.

1.36 g (0.027 mole) of 50% sodium hydride was added in portions to a solution of 7.06 g (0.023 mole) of 3-(2,6-di-tertiary-butylcyclohexadienon-4-ylidenamino)phenol in a mixture of 50 ml 1,2-dimethoxyethane and 10 ml of dimethylacetamide. Three ml (0.027 mole) of ethyl bromoacetate was then added in portions. The reaction mixture was stirred at room temperature for about one hour, and a solution of 1.3 g of sodium hydroxide in 12 ml of water was added. After about 30 minutes the reaction mixture was acidified with hydrochloric acid and was extracted with diethyl ether. The ether extract was washed with a saturated sodium chloride solution and evaporated to give an orange solid. This solid was recrystallized from a mixture of benzene and hexane to give 6.2 g of an orange solid, m.p. 161°–162° C. One g of this material was recrystallized from a mixture of 10 ml of ethanol and 5 ml of water to give 0.8 g of orange crystalline 3-(2,6-di-tertiary-butylcyclohexadienon- 4-ylideneamino)phenoxyacetic acid, m.p. 163°–165° C. Analysis: Calculated for $C_{22}H_{27}NO_4$: % C, 71.5; %}{, 7.4; % N, 3.8; Found: % C, 71.8; %}{, 7.2; % N, 3.7.

A mixture of 5.0 g of 3-(2,6-di-tertiary-butylcyclohexadienon- 4-ylideneamino)phenoxyacetic acid, 250 ml of ethanol and 10 mg of 5% palladium on charcoal catalyst was placed on a Paar apparatus. Hydrogenation was complete after five hours. The reaction mixture was filtered to remove the catalyst and the filtrate was evaporated to give a thick brown oil. The oil was dissolved in 20 ml of benzene, filtered, diluted with 20 ml of cyclohexane and 10 ml of hexane, and chilled to give 1.4 g of light tan crystalline 3-(3,5-di-tertiary-butyl-4-hydroxyanilino)phenoxyacetic acid, m.p. 127°–127.5° C. Analysis: Calculated for $C_{22}H_{29}NO_4$: % C, 71.1; % H, 7.9; % N, 3.8; Found: % C, 70.3; % H, 7.6; % N, 3.7.

EXAMPLE 43

A suspension of 6.0 g (0.027 mole) of 2,6-di-tertiary-butyl-p-benzoquinone, 3.3 g (0.020 mole) of p-aminocinnamic acid, 15 ml of tetrahydrofuran and 0.3 ml of boron trifluoride etherate was heated at reflux for one hour. The reaction mixture was dissolved in a minimum amount of methylene chloride, and was diluted to a final volume of 700 ml with diethyl ether. The ether solution was washed first with cold 10% hydrochloric acid and then with brine, and was then dried over magnesium sulfate and evaporated almost to dryness. The residue was diluted with 300 ml of hexane and evaporated almost to dryness before being diluted with 500 ml of warm hexane. The mixture was allowed to cool to room temperature before being filtered to give 5.8 g of a bright red powder. One g of this material was recrystallized from a mixture of 15 ml of benzene and 3 ml of hexane to give 0.5 g of red crystalline 4-(2,6-di-tertiary-butylcyclohexadienon-4-ylideneamino)cinnamic acid, m.p. 216°–217.5° C. Analysis: Calculated for $C_{23}H_{27}NO_3$; % C, 75.6; % H, 7.4; % N, 3.8; Found: % C, 75.9; % H, 7.5; % N, 3.8.

A mixture of 2.0 g of 4-(2,6-di-tertiary-butylcyclohexadienon- 4-ylideneamino)cinnamic acid, 100 ml of methanol, 0.5 ml of concentrated hydrochloric acid and 2 g of zinc powder was stirred for ten minutes. The mixture was filtered and the filtrate was evaporated to give a yellow gummy solid. This material was recrystallized from a mixture of 15 ml of benzene, 4 ml of hexane and 2 ml of cyclohexane to give 0.4 g of yellow granular 4-(3,5-di-tertiary-butyl- 4-hydroxyanilino)cinnamic acid, m.p. 199°–200° C. Analysis: Calculated for $C_{23}H_{29}NO_3 \cdot \tfrac{2}{3}C_6H_6$: % C, 77.4; % H, 7.9; % N, 3.3; Found: % C, 77.2; % H, 7.8; % N, 3.3.

EXAMPLE 44

A suspension of 5.0 g (0.0147 mole) of 2,6-di-tertiary-butyl-4-(3'-carboxyphenylimino)-2,5-cyclohexadien- 1-one (prepared in Example 2) in 15 ml of benzene and 2.5 ml of thionyl chloride was heated at reflux until gas evolution ceased. The solution was evaporated, and was evaporated twice more following additions of benzene. The resulting acid chloride was added dropwise to a solution of 5.5 g sodium trifluoromethanesulfonamide in 25 ml of 1,2-dimethoxyethane. The solvent was evaporated with a stream of nitrogen to give a yellow solid. This solid was stirred with 200 ml of tetrahydrofuran and was then filtered to remove insoluble material. The filtrate was hydrogenated for 16 hours on a Paar apparatus using 0.5 g of 5% palladium on charcoal as the catalyst. The catalyst was removed by filtration and the filtrate was evaporated to give a dark brown oil. The oil was dissolved in 25 ml of water. This solution was added to a mixture of 5.0 ml of 10% hydrochloric acid, water and ice to give 6.7 g of a white solid. This solid was recrystallized from a mixture of 70 ml of ethanol and 20 ml of water to give 3 g of white crystalline N-[3-(3,5-di-tertiary-butyl-4-hydroxyanilino)benzoyl] trifluoromethanesulfonamide, m.p. 234°–234.5° C. Analysis: Calculated for $C_{22}H_{27}F_3N_2O_4S$: % C, 55.9; % H, 5.8; % N, 5.9; Found: % C, 56.1; % H, 5.8; % N, 5.9.

EXAMPLE 45

A mixture of 13.2 g (0.10 mole) of 3-amino-4-hydroxybenzoic acid, 22.0 g (0.10 mole) of 2,6-di-tertiary-butyl-p-benzoquinone, 25 ml of tetrahydrofuran and 1 ml of boron trifluoride etherate was heated at a gentle reflux for about 20 minutes by which time a thick precipitate had formed. The reaction mixture was diluted with 50 ml of ethanol and filtered to obtain 20.9 g of an orange solid, m.p. 248°–250° C. Six g of this material was recrystallized from a mixture of 250 ml of ethanol and 70 ml of water to give 3.4 g of red granular 3-(2,6-di-tertiary-butylcyclohexadienon-4-ylideneamino)-4-hydroxybenzoic acid, m.p. 275°–276° C. Analysis: Calculated for $C_{21}H_{25}NO_4$: % C, 71.0; % H, 7.1; % N, 4.0; Found: % C, 71.4; % H, 7.1; % N, 3.8.

A mixture of 5.0 g of 3-(2,6-di-tertiary-butylcyclohexadienon- 4-ylideneamino)-4-hydroxybenzoic acid, 0.05 g of 5% palaldium on charcoal catalyst, 250 ml of ethanol and 50 ml of tetrahydrofuran was placed on a Paar apparatus. Hydrogen uptake was complete in about 10 minutes. The reaction mixture was filtered to remove catalyst. The filtrate was evaporated to give a tan solid which was recrystallized from a mixture of 40 ml of ethanol and 15 ml of water to give 3.2 g of reddish tan granular 3-(3,5-di-tertiary-butyl-4-hydroxyanilino)-4-hydroxybenzoic acid, m.p. 254.5°–255° C. (dec). Analysis: Calculated for $C_{21}H_{27}NO_4$: % C, 70.6; % H, 7.6; % N, 3.9; Found: % C, 71.0; % H, 7.6; % N, 4.1.

What is claimed is:
1. A compound of the formula

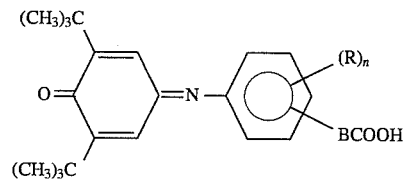

wherein R is hydrogen, lower alkyl, lower alkoxy, lower alkylthio, hydroxy, halogen, amino or lower acylamino; n is 0, 1 or 2, with-the proviso that when n is 2, the R substituents combined contain no more than 6 carbon atoms; and B is a carbon-carbon bond, lower alkylene, lower alkenylene, lower alkylene containing one ether or thioether link in the alkylene chain, or

with the proviso that —BCOOH is bonded to the phenyl ring ortho or meta when B is a carbon-carbon bond.